(12) United States Patent
Klostermann et al.

(10) Patent No.: US 8,428,745 B2
(45) Date of Patent: *Apr. 23, 2013

(54) TELEMETRY PROTOCOL FOR ULTRA LOW ERROR RATES USEABLE IN IMPLANTABLE MEDICAL DEVICES

(75) Inventors: Daniel Joseph Klostermann, Valencia, CA (US); Mizanur Rahman, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,450

(22) Filed: Aug. 14, 2012

(65) Prior Publication Data

US 2012/0310306 A1   Dec. 6, 2012

Related U.S. Application Data (63) Continuation of application No. 11/215,365, filed on Aug. 30, 2005, now Pat. No. 8,265,768.

(51) Int. Cl.
*A61N 1/08* (2006.01)
(52) U.S. Cl.
USPC ............. 607/60; 607/30; 607/31; 607/32
(58) Field of Classification Search .......... 714/748–751, 714/758; 702/189; 375/399.02; 607/30–32, 607/60

See application file for complete search history.

(56) References Cited

U.S. PATENT DOCUMENTS

| | | | |
|---|---|---|---|
| 3,646,940 A | 3/1972 | Timm et al. | 128/421 |
| 3,724,467 A | 4/1973 | Avery et al. | 128/418 |
| 3,822,708 A | 7/1974 | Zilber | 128/419 R |
| 5,122,875 A | 6/1992 | Raychaudhuri et al. | 358/133 |
| 5,677,918 A | 10/1997 | Tran et al. | 371/32 |
| 6,173,431 B1 * | 1/2001 | Rittle | 714/778 |
| 6,181,969 B1 | 1/2001 | Gord | 607/59 |
| 6,456,875 B1 * | 9/2002 | Wilkinson et al. | 607/2 |
| 6,516,227 B1 | 2/2003 | Meadows et al. | 607/46 |
| 6,811,533 B2 | 11/2004 | Lebel et al. | 600/300 |
| 7,127,654 B2 | 10/2006 | Jalali et al. | 714/748 |
| 7,389,463 B2 | 6/2008 | Ramaswamy et al. | 714/752 |
| 7,539,538 B2 | 5/2009 | Parramon et al. | 607/2 |
| 7,586,948 B2 | 9/2009 | Hiddink et al. | 370/473 |
| 7,606,288 B2 | 10/2009 | Prestwich et al. | 375/146 |
| 2006/0268961 A1 * | 11/2006 | Prestwich et al. | 375/146 |

FOREIGN PATENT DOCUMENTS

EP   1014730   12/1999

\* cited by examiner

*Primary Examiner* — Rex R Holmes

(74) *Attorney, Agent, or Firm* — Wong, Cabello, Lutsch, Rutherford, & Brucculeri, LLP (57) ABSTRACT

A telemetry protocol for an implantable medical device is disclosed. The sending device forms a block of information to be telemetered to the receiving device, including a header, a message, and an error detection data (CRC1). The entirety of the block is divided into smaller packets of a predetermined size. Each packet has a CRC computed for it (CRC2), and is sent to the receiving device, which deduces a CRC2 and compares it with the appended CRC2. If not valid, that packet is again requested to be resent. If valid, the next packet is requested to be sent, its CRC2 checked, etc., until all packets are received and verified. The receiving device then discards the CRC2s to reconstitute the original block. The receiving device then deduces CRC1 and compares it with the CRC1 appended to the block. If valid, the block is accepted, and if not, the procedure is repeated.

27 Claims, 9 Drawing Sheets

TELEMETRY PROTOCOL FOR ULTRA LOW ERROR RATES USEABLE IN IMPLANTABLE MEDICAL DEVICES

CROSS-REFERENCE TO RELATED APPLICATIONS

This is a continuation of U.S. patent application Ser. No. 11/215,365, filed Aug. 30, 2005 (now U.S. Pat. No. 8,265, 768), which is incorporated herein by reference in its entirety, and to which priority is claimed.

FIELD OF THE INVENTION

The present invention relates generally to implantable medical devices, e.g., pulse generators used in a Spinal Cord Stimulation (SCS) systems or other types of neural stimulation systems. More particularly, the present invention relates to a telemetry protocol for communication between an external component and an implantable stimulator device. The invention provides very low error rates and also preferably minimizes power consumption in the implantable stimulator device.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. patent application Ser. No. 11/177,503, filed Jul. 8, 2005, which is incorporated herein by reference in its entirety.

Spinal cord stimulation is a well-accepted clinical method for reducing pain in certain populations of patients. An SCS system typically includes an Implantable Pulse Generator (IPG) or Radio-Frequency (RF) transmitter and receiver, electrodes, at least one electrode lead, and, optionally, at least one electrode lead extension. The electrodes, which reside on a distal end of the electrode lead, are typically implanted along the dura of the spinal cord, and the IPG or RF transmitter generates electrical pulses that are delivered through the electrodes to the nerve fibers within the spinal column. Individual electrode contacts (the "electrodes") are arranged in a desired pattern and spacing to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the IPG or RF transceiver is implanted. Alternatively, the electrode lead may directly connect with the IPG or RF transceiver. For examples of other SCS systems and other stimulation systems, see U.S. Pat. Nos. 3,646,940 and 3,822,708, which are hereby incorporated by reference in their entireties. Of course, implantable pulse generators are active devices requiring energy for operation, such as is provided by an implanted battery or an external power source.

Figure 1:
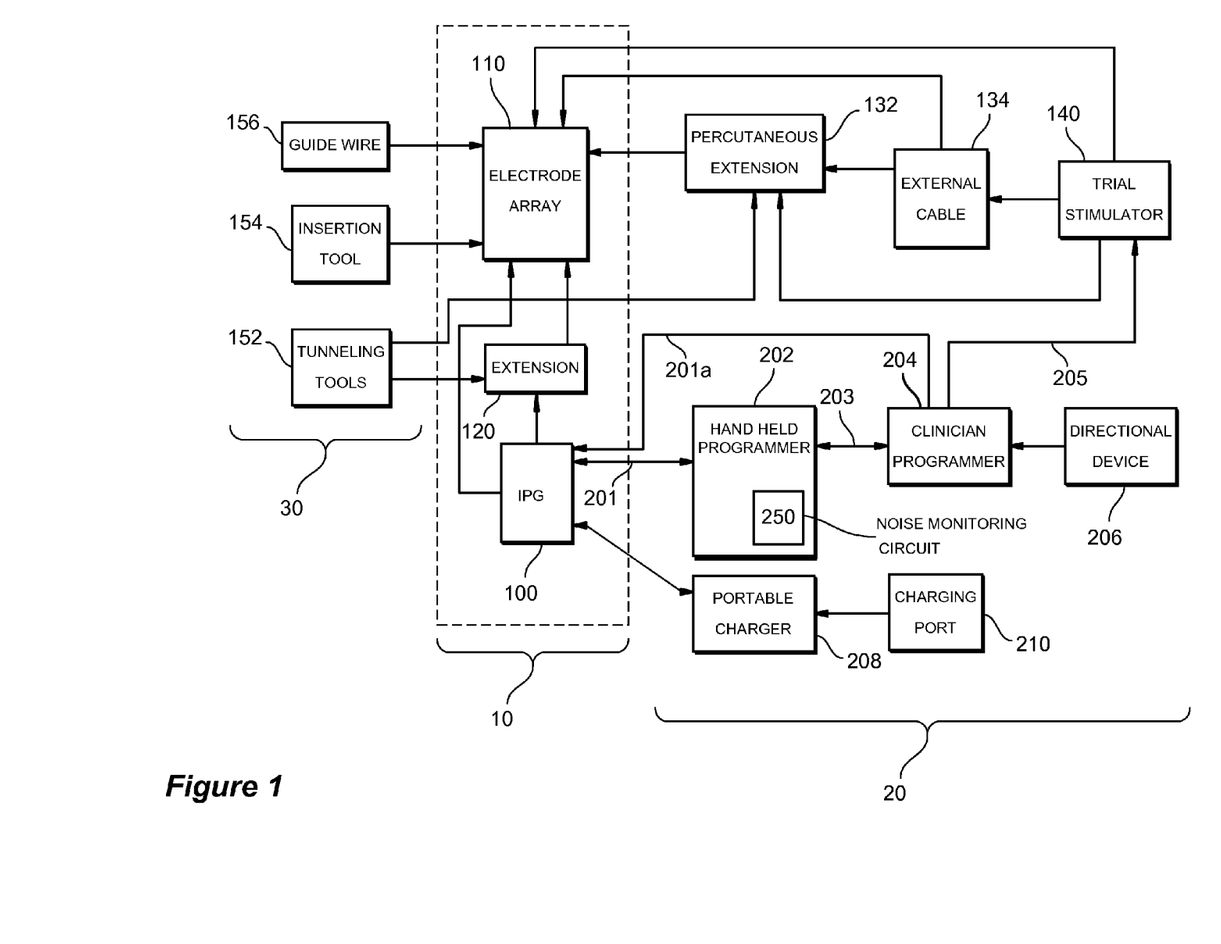
FIG. 1 shows a block diagram that illustrates exemplary implantable, external, and surgical components of a spinal cord stimulation (SCS) system that employs an implantable medical device in accordance with the present invention.
Figure 2:
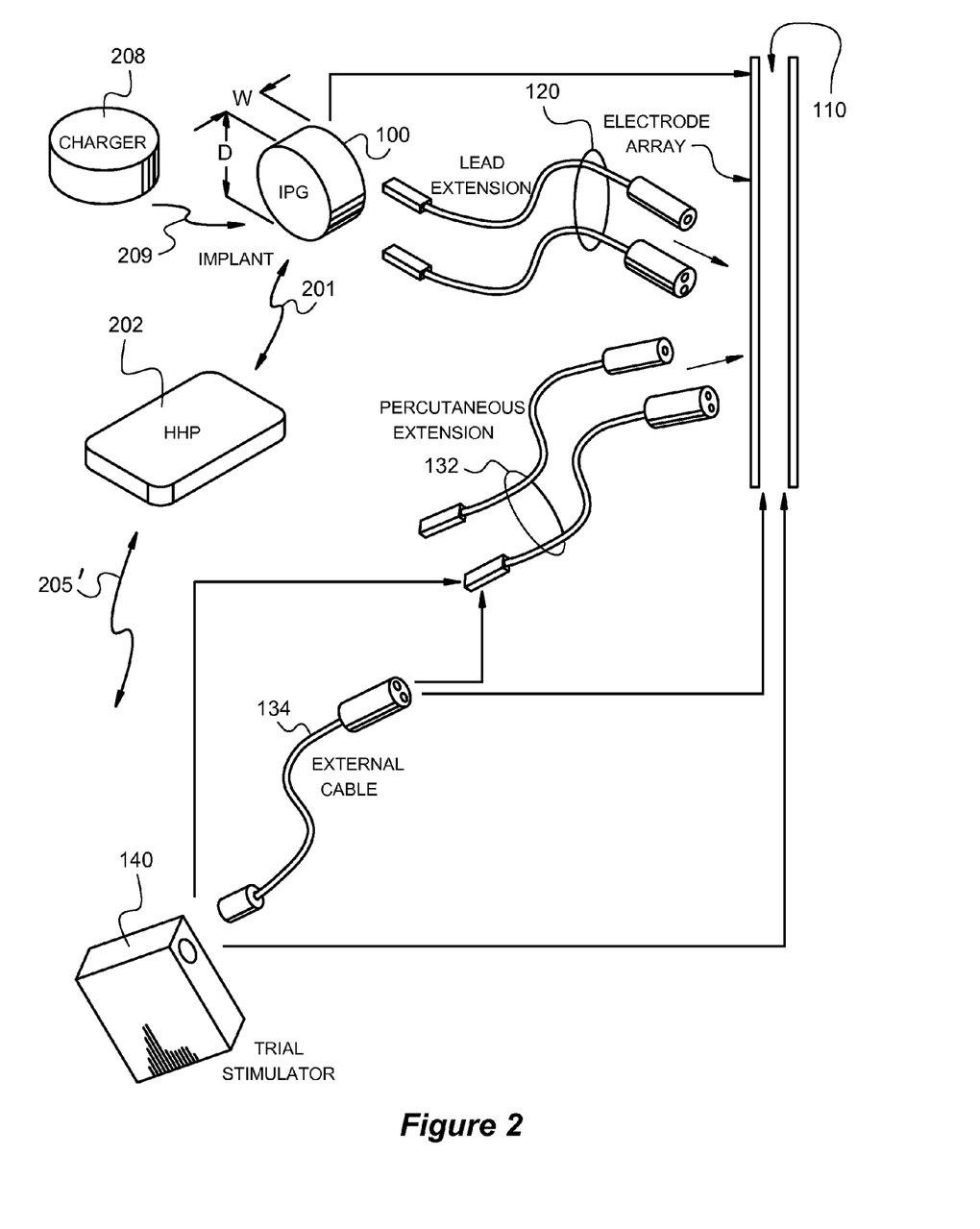
FIG. 2 shows various components of the SCS system of FIG. 1.
Figure 3:
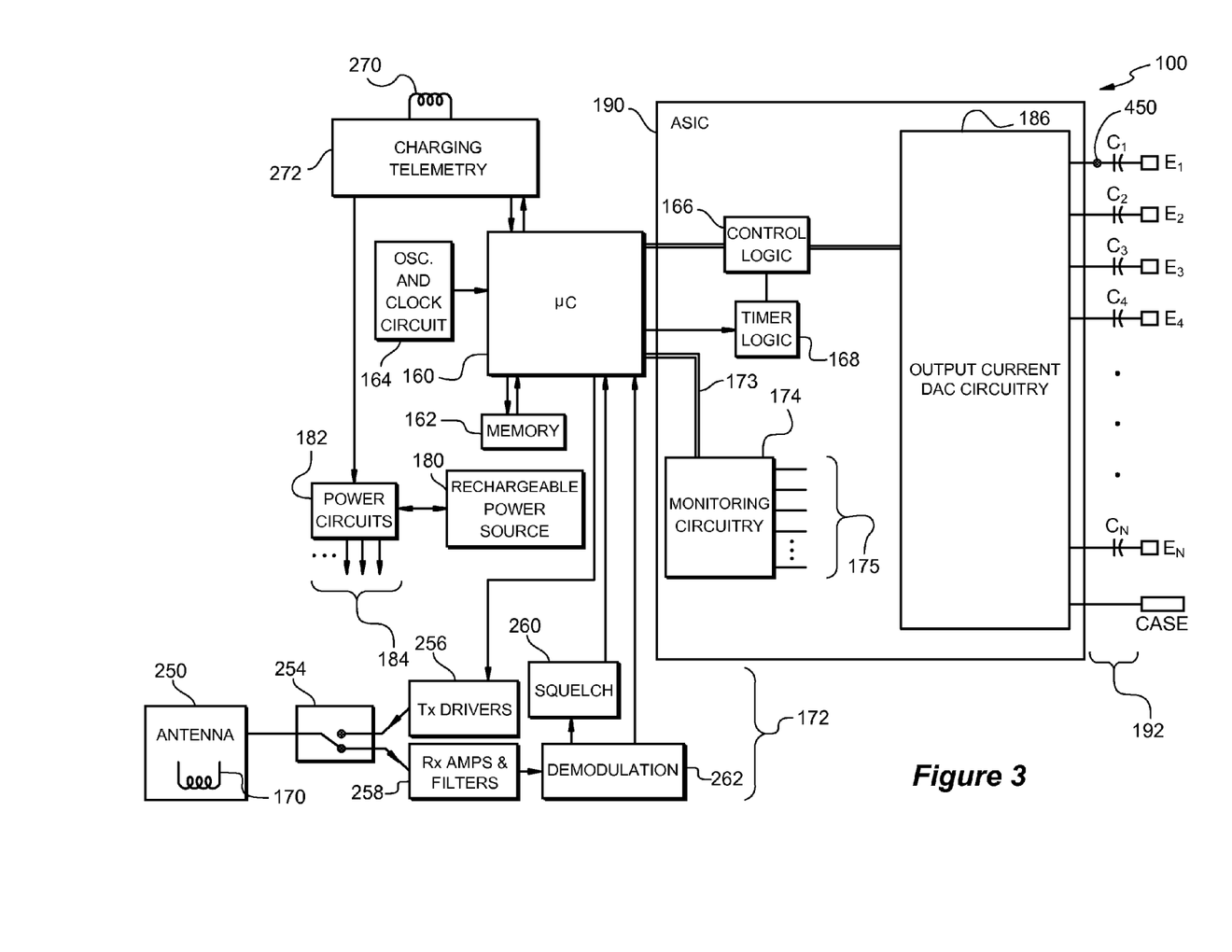
FIG. 3 shows a block diagram that illustrates the main components of one embodiment of an implantable stimulator device in which the invention can be used.

FIGS. 1-3 introduce various components of an exemplary SCS system, although further details will be explained more fully later. As particularly relevant to the present discussion, the SCS components comprise implantable components 10 (i.e., components implantable or implanted into a patient requiring therapy) and external components 20 (i.e., components external to the patient but which work in conjunction with the internal components 10). As seen in FIG. 1, the implantable components 10 include an implantable pulse generator (IPG) 100, which may comprise a rechargeable, multi-channel, telemetry-controlled, pulse generator. The external components 20 include a remote control 202, otherwise known as a hand-held programmer (HHP) 202, which may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set within prescribed limits. Detailed, system-level programming of the IPG 100 may additionally be accomplished through the use of an external clinician's programmer (CP) 204, which may also be hand-held and which may be coupled to the IPG 100 directly via an RF link 201a or indirectly using the HHP 202 as an intermediary. These RF links 201, 201a are preferably two-way links that can be used to send data to (i.e., control) the IPG 100, or to receive data from the IPG 100.

Such RF telemetry between the HHP 202 or CP 204 and the IPG 100 is supported via circuitry in the IPG 100, as shown in FIG. 3. Among other components and circuitry which will be described in further detail later, the IPG 100 comprises RF-telemetry circuitry 172, which receives RF telemetry data from the external components 20 (such as desired IPG operating parameters) and which sends RF telemetry data to the external components 20 (e.g., to allow the IPG 100's operating parameters to be verified, to allow the IPG 100's identification number to be reported, etc.).

Figure 5:
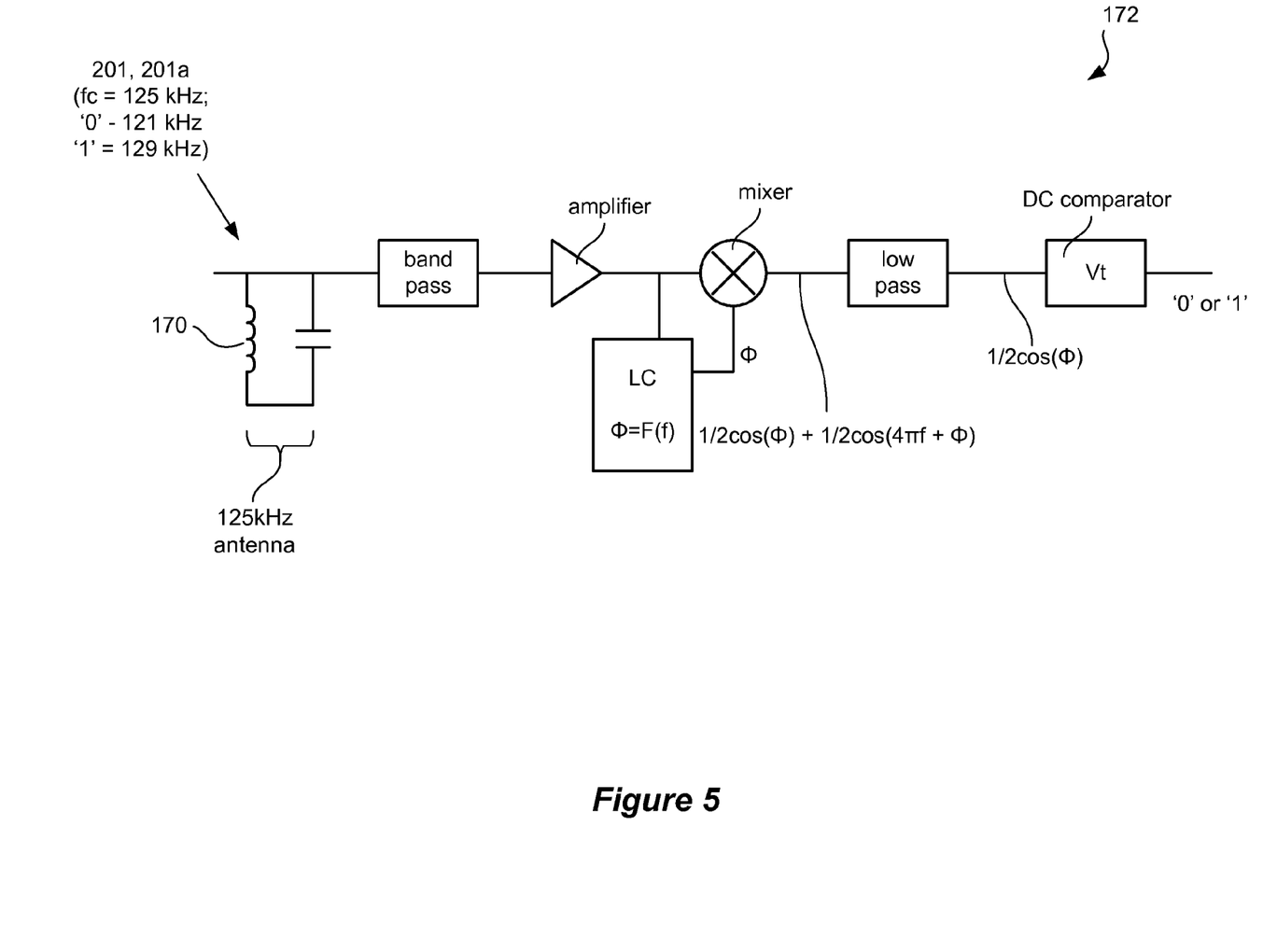
FIG. 5 shows the RF-telemetry circuitry used in an exemplary implantable stimulator, and specifically shows the demodulation circuitry.

In recognition of the fact that the RF telemetry through links 201 and 201a would generally comprise use of a modulated carrier, RF-telemetry circuitry 172 would preferably include demodulator circuitry 262. Exemplary frequency demodulation circuitry useable in an IPG 100, as well as other components of the RF-telemetry circuitry 172, is shown in FIG. 5. What is shown for simplicity is an analog FM demodulation circuit, but one skilled in the art will recognize that it can be implemented digitally as well, and preferably would be implemented digitally in an implantable stimulator application. (In a digital implementation, some of the circuit elements shown would not be used, such as the LC circuit and mixer).

The operation of the demodulation circuitry is known to one skilled in the art, and hence is only briefly described. Essentially, data is sent to the demodulation circuitry (e.g., via RF links 201, 201a) as a sequence of bits represented by a variance in frequency (121 kHz, 129 kHz) from a center carrier frequency ($f_c$=125 kHz). After passing the received signal through a band pass filter to remove frequencies outside of the frequency range of interest, a phase shift ($\phi$) is induced in the received signal via an LC circuit for example, in which the phase shift is a function of the frequency of the received signal. By mixing the phase shifted signal with the original received signal, and sending the result through a low pass filter to remove high-frequency components, a voltage (proportional to $\frac{1}{2}\cos(\phi)$) is generated which is compared to a threshold to determine whether the received signal comprised a 121 kHz signal (a logical '0') or a 129 kHz signal (a logical '1'). As noted earlier, digital demodulation is logical in an implantable medical device application, and could for example comprise use of the QFAST RF protocol, which supports bi-directional telemetry at, e.g., 8 Kbits/second. (QFAST stands for "Quadrature Fast Acquisition Spread Spectrum Technique," and represents a known and viable approach for modulating and demodulating data).

It should be obvious that the telemetry between the IPG 100 and the HHP 202, the CP 204, or any other external device, is critical and should occur with the lowest error rates possible. That is to say, when sending bits of information to or from the IPG 100, precautions should be taken to ensure that transmission errors, if they occur, are detected and remedied. This is particularly important for communications sent to IPG 100, which can potentially affect the treatment received by the patient.

Figure 6:
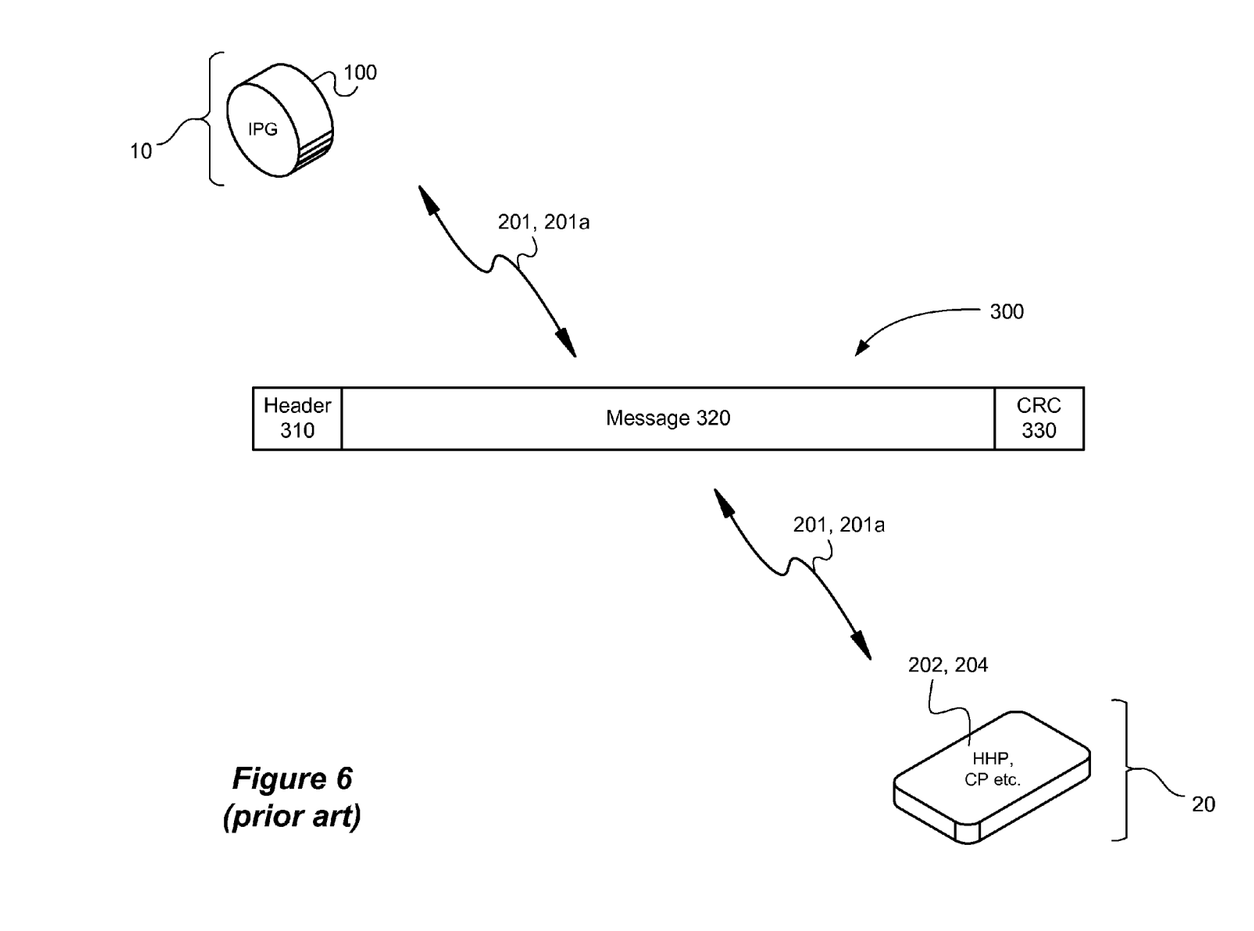
FIG. 6 shows the telemetry of a block of information, including a header, a message, and a CRC, between an external component and an implantable stimulator device according to the prior art.

In this regard, it has been known in the art of implantable stimulator devices to use error detection algorithms, such as is illustrated in FIG. 6. As shown, data is telemetered to and from the IPG 100 via RF links 201, 201a in the form of blocks 300. The blocks 300 typically comprise in sequence a header 310, a message 320, and an error code 330. The header 310 may include code understood by the receiving device as indicative of the beginning of a block 300, and may include other information such as the length or type of the message 320 to follow, the ID number of the IPG, etc. The message 320 comprises the main data "payload" of the block 300, and can comprise for example the stimulation parameters (e.g. electrode polarity, amplitude, pulse rate, pulse width, etc.) as sent by the HHP 202 to program the IPG 100 (or as reported back from the IPG 100 to the HHP 202 after programming). The message 320 can be a fixed number of bytes, or may be variable in size.

The error code 330 is appended to the end of the block 330 and as its name would suggest is used in determining the possibility of a transmission error. In the example shown in FIG. 6, the error code 330 comprises a Cyclic Redundancy Code (i.e., a CRC) 330. CRCs such as CRC 330 are well known in the art of telemetry, and hence are only briefly explained.

A CRC comprises a remainder of the data (i.e., the hexadecimal number comprising the header 310 plus message 320) when divided by a particular hexadecimal "polynomial" used in accordance with the particular CRC scheme at hand. For example, one such well known CRC polynomial is 0x1021, which denotes the hexadecimal number '1021.' ('0x' informs in C programming that the number to follow is a hexadecimal number). Thus, on the sending end of the telemetry, the sending device (e.g., HHP 202) compiles the header 310 and message 320, and divides that data by $0x10^{21}$. The remainder of that division comprises the CRC 330. The sending device then appends the CRC 330 to the header 310 and message 320 and sends it to the receiving device as shown.

On the receiving end, the receiving device (e.g., IPG 100) likewise assesses the data (310 and 320) and computes a CRC 330 using the same polynomial. If the CRC 330 does not indicate a match, the receiving device will deduce that a transmission error occurred, e.g., a logic '0' bit was inadvertently received as a '1' bit, etc. In such a circumstance, the receiving device can take an appropriate corrective action, such as discarding the block 300 it received, or better yet requesting the sending device to resend the block in question. In any event, the point is that the CRC 330 comprises a means for assessing potential errors in the telemetry between the sending and receiving devices. Moreover, because of the mathematics involved, the CRC methodology has a low probability for error—meaning that it will flag transmission errors with a low probability of being incorrect (e.g., indicating transmission was not faulty when it actually was).

But CRCs, and other error detection algorithms for that matter, can fail. To cite a simple example, there could be four bits which are erroneously transmitted in the data which effectively cancel each other out in the CRC analysis, with the effect being that the CRCs will match on the sending and receiving ends despite the transmission error (i.e., a false positive).

Although the probabilities of a CRC failure are generally very low, such failure probabilities can be significant in an implantable stimulator device application. In such an application, the effect of an error detection failure can mean that the IPG 100 is not properly programmed, and hence that the patient will not receive the proper therapy as prescribed. Although IPGs typically employ safeguards to ensure that erroneous programming would not injure a patient, improper programming can have significant health consequences. It therefore behooves the designer of such systems to reduce the failure rates of error detection algorithms to the lowest levels possible.

Moreover, error detection algorithms, even when functioning properly, are still not ideal as implemented in the unique context of implantable stimulator devices. In this regard, note that an IPG must ultimately draw power to function and to provide stimulation pulses to the patient in which it is implanted. Regardless of whether an IPG is powered by a non-rechargeable battery, or is powered by a battery rechargeable via an RF energy source (e.g., charger 208, FIG. 1), or is solely powered via an RF energy source, power consumption in an IPG is preferably kept to a minimum. For example, in the case of an IPG with a rechargeable battery, lower power consumption equates to longer periods in which the IPG can be used to provide stimulation between charges.

Error detection algorithms as implemented in implantable stimulator devices are not generally considerate of such power constraints. For example, consider the transmission from an HHP 202 to an IPG 100 of a block 300 having a message 320 which is relatively long—comprising say 100 or more bytes of information. Suppose further that the message 320 as transmitted contains a single bit error, as reflected by the CRC comparison made by the receiving device. In other words, only a single bit out of approximately 800 bits in the block 300 is erroneous. While it is good that such an error has been detected, the reality is that the IPG 100 has had to receive the entirety of the block 300 to make this determination, and to initiate a correction action such as requesting a resend of the block. But receipt of such erroneous data is wasteful of IPG power. Specifically, to initially receive the erroneous block 300, the IPG 100 must power on the RF-telemetry circuitry 172 (FIG. 5) so that the bits in the telemetered block can be deciphered by the demodulation circuitry. The RF telemetry circuitry 172 in the IPG 100 generally draws significant amounts of power, and therefore keeping it powered to receive a long ultimately-erroneous message is, in retrospect, wasteful. It is also regrettable that time is wasted through this procedure, as the IPG 100, or at least the telemetry circuitry, is tied up receiving the long ultimately-erroneous message.

Accordingly, the implantable stimulator art, such as the IPG or SCS system art, would benefit from telemetry techniques for implantable stimulator devices which provide low transmission error rates and which also preferably minimize power consumption in the IPG. Such solutions are provided herein.

SUMMARY

An improved telemetry protocol for an implantable medical device (e.g., an implantable stimulator device) system is disclosed that reduces error rates and is considerate of power consumption. In one embodiment, the sending device (such as the HHP 202 or CP 204) forms a block of information to be telemetered to the receiving device (e.g., an IPG 100) in a typical fashion, including a header, a message, and an error detection code such as a CRC for that data. This CRC of the block, called CRC1, is preferably computed using a first CRC polynomial. Then, the entirety of the block, including the header, message, and CRC1, is divided into smaller packets of a predetermined byte size. Each packet, regardless of its contents (i.e., regardless of whether it contains the header, the message, or the CRC1, or portions of these), has a CRC computed for it. The CRCs of the packets, called CRC2s, are preferably (but not necessarily) computed using a second CRC polynomial different from the first. So formed, each packet with its appended CRC2 is sent to the receiving device, which deduces a CRC2 and compares it with the appended CRC2. If not valid, that packet is again requested to be resent. If valid, the next packet is requested to be sent, its CRC2 checked, etc., until all packets are received and verified. At this point, the receiving device discards the CRC2s from the received packets and reconstitutes the original block (including the header, message, and CRC1). The receiving device then deduces CRC1 and compares it with the CRC1 appended to the block. If valid, the block is accepted, and if not, the information is retransmitted and the procedure is repeated for the block.

Through use of this protocol, improved telemetry error rates and improved power and time savings in the receiving device are achieved. Improved error rates result from the redundancy involved in calculating two CRCs (CRC1 and CRC2), one on the whole of the block and one on the various packets that comprise the block. Use of different CRC polynomials at these two levels of assessment further reduce error rates, because one polynomial might catch errors another polynomial would miss. However, this is not strictly necessary, and the same CRC polynomial can be used for both CRC1 and CRC2.

Power and time savings result because an entire block need not be received and assessed by the receiving device before a determination of transmission error is made. Instead, at least some transmission errors can be assessed, and remedied, at the packet level, as opposed to the block level. If an error is determined at the packet level (e.g., via the CRC2 for the packet), only that packet need be retransmitted, rather than the longer block. As a result, the receiving circuitry (e.g., the RF-telemetry circuitry 172 of FIG. 5) will be powered on less, which saves significant power in the IPG 100.

BRIEF DESCRIPTION OF THE DRAWINGS

The above and other aspects of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing the telemetry-based aspects of the invention, the circuitry, structure, and function of an implantable stimulator device in which the disclosed telemetry-based improvements can be used is set forth for completeness. The disclosed implantable stimulator device may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from power-saving telemetry procedures. For example, the present invention may be used as part of a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc.

Turning first to FIG. 1, a block diagram is shown that illustrates the various components of an exemplary SCS system in which the invention may be used. These components may be subdivided into three broad categories: implantable components 10, external components 20, and surgical components 30. As seen in FIG. 1, the implantable components 10 include an implantable pulse generator (IPG) 100, an electrode array 110, and (as needed) a lead extension 120. The extension 120 may be used to electrically connect the electrode array 110 to the IPG 100. In an exemplary embodiment, the IPG 100, described more fully below in connection with FIG. 3 or 4, may comprise a rechargeable, multi-channel, telemetry-controlled, pulse generator housed in a rounded high-resistivity titanium alloy case to reduce eddy current heating during the inductive charging process. The IPG 100 may provide electrical stimulation through a multiplicity of electrodes, e.g., sixteen electrodes $E_1$ through $E_{16}$, included within the electrode array 110.

In this regard, the IPG 100 may include stimulating electrical circuitry ("stimulating electronics"), a power source, e.g., a rechargeable battery, and a telemetry system, the latter of which is particularly relevant to embodiments of the disclosed invention. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted and any trial stimulation period is complete, the lead system 110 and lead extension 120 are intended to be permanent. In contrast, the IPG 100 may be replaced when its power source fails or is no longer rechargeable.

As seen best in FIG. 2, and as also illustrated in FIG. 1, the electrode array 110 and its associated lead system typically interface with the implantable pulse generator (IPG) 100 via the lead extension system 120 just mentioned. The electrode array 110 may also be connected to an external trial stimulator 140, through the use of a percutaneous lead extension 132 and/or an external cable 134. The external trial stimulator 140 typically includes the same or similar pulse generation circuitry as does the IPG 100, and is used on a trial basis, e.g., for 7-10 days, after the electrode array has been implanted and prior to implantation of the IPG 100, to test the effectiveness of the stimulation that is to be provided.

Still with reference to FIGS. 1 and 2, and as noted earlier, a hand-held programmer (HHP) 202 may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set by a patient or clinician within prescribed limits. The HHP 202 may also be linked with the external trial stimulator 140 through another link 205', e.g., an infra red link. Detailed programming of the IPG 100 is preferably accomplished through the use of an external clinician's programmer (CP) 204 (FIG. 1), which may also be hand-held and which may be coupled to the IPG 100 directly via link 201a or indirectly through the HHP 202. An external charger 208, non-invasively coupled with the IPG 100 through link 209, e.g., an inductive link, allows energy stored or otherwise made available to the charger 208 to be coupled into the rechargeable battery housed within the IPG 100, as explained further below.

Turning next to FIG. 3, a block diagram is shown that illustrates the main components of one embodiment of an implantable pulse generator (IPG) 100 in which embodiments of the invention may be used. As seen in FIG. 3, the IPG includes a microcontroller (μC) 160 connected to memory circuitry 162. The μC 160 typically comprises a microprocessor and associated logic circuitry, which in combination with control logic circuits 166, timer logic 168, and an oscillator and clock circuit 164, generate the necessary control and status signals which allow the μC 160 to control the operation of the IPG in accordance with a selected operating program and stimulation parameters.

The operating program and stimulation parameters are telemetered to the IPG 100, where they are received via antenna 250 (which may include a coil 170 and/or other antenna components), processed, e.g., via RF-telemetry circuitry 172, and may be stored, e.g., within the memory 162. As noted earlier, the RF-telemetry circuitry 172 demodulates the signal it receives from the HHP 202 or CP 204 to recover the operating program and/or the stimulation parameters. More specifically, telemetry received at coil 170 is met by an LC-tuned antenna 250, where it passes through a transmit/receive switch 254 to amplifiers and filters 258 (see also FIG. 5). From there, the received signals are demodulated (262) using Frequency Shift Keying (FSK) demodulation for example, and the now-digitized and demodulated data is then sent to the microcontroller 160 for processing and/or eventual storage. When RF-telemetry circuitry 172 is used to transmit information to the HHP 202 or CP 204 to report in some fashion on its status, the microcontroller 160 sends relevant data to transmission drivers 256, where the data is modulated and amplified for transmission. The transmit/receive switch 254 would then be set to communicate with the transmission drivers 256, which in turn drive the data to the antenna 250 to be broadcast.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes $E_1 \ldots E_N$, and the like. Informational data sensed through the monitoring circuit 174 may be sent to a remote location external to the IPG (e.g., a non-implanted location) through telemetry circuitry 172 via coil 170.

The operating power for the IPG 100 may be derived from a rechargeable power source 180, which may comprise a lithium-ion or lithium-ion polymer battery, for example. The rechargeable battery 180 provides an unregulated voltage to power circuits 182. The power circuits 182, in turn, generate the various voltages 184, some of which are regulated and some of which are not, as needed by the various circuits located within the IPG 100. In a preferred embodiment, the battery 180 is charged by an electromagnetic field created by an external portable charger 208 (FIG. 1). When placed near the IPG 100 (e.g., centimeters away), an electromagnetic field emanating from the portable charger 208 induces a current in charging coil 270 (even through a patient's skin). This current is then rectified and regulated to charge the battery 180. Further associated with the charging circuitry is charging telemetry circuitry 272, which is used for example by the IPG 100 to report back to the portable charger 208 when the battery is full, and thus when portable charger can be shut off.

In one exemplary embodiment, any of the N electrodes may be assigned to up to k possible groups or "channels." In one preferred embodiment, k may equal four. Moreover, any of the N electrodes can operate, or be included in, any of the k channels. The channel identifies which electrodes are selected to synchronously source or sink current to create an electric field in the tissue to be stimulated. Amplitudes and polarities of electrodes on a channel may vary, e.g., as controlled by the HHP 202. External programming software in the CP 204 is typically used to set parameters including electrode polarity, amplitude, pulse rate and pulse width for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a bipolar mode or multipolar mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode contact may be programmed to one of several discrete current levels, e.g., between 0 to 10 mA in steps of 0.1 mA. Also, the pulse width of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 1000 Hz. Other programmable features can include slow start/end ramping, burst stimulation cycling (on for X time, off for Y time), and open or closed loop sensing modes.

The stimulation pulses generated by the IPG 100 may be charge balanced. This means that the amount of positive charge associated with a given stimulus pulse is offset with an equal and opposite negative charge. Charge balance may be achieved through coupling capacitors $C_X$, which provide a passive capacitor discharge that achieves the desired charge-balanced condition. Alternatively, active biphasic or multiphasic pulses with positive and negative phases that are balanced may be used to achieve the needed charge balanced condition.

In short, the IPG 100 is able to individually control the currents at the N electrodes. Controlling the output current Digital-to-Analog Current (DAC) circuitry 186 using the microcontroller 160, in combination with the control logic 166 and timer logic 168, allows each electrode contact to be paired or grouped with other electrode contacts, including the monopolar case electrode, to control the polarity, amplitude, rate, pulse width and channel through which the current stimulus pulses are provided.

As shown in FIG. 3, much of circuitry included within the IPG 100 may be realized on a single application specific integrated circuit (ASIC) 190. This allows the overall size of the IPG 100 to be quite small, and readily housed within a suitable hermetically-sealed case. The IPG 100 may include N feedthroughs to allow electrical contact to be individually made from inside of the hermetically-sealed case with the N electrodes that form part of the lead system outside of the case.

As noted earlier, in use, the IPG 100 may be placed in a surgically-made pocket, e.g., in the abdomen or just at the top of the buttocks, and detachably connected to the lead system (comprising optional lead extension 120 and electrode array 110). While the lead system is intended to be permanent, the IPG 100 may be replaced should its power source fail, or for other reasons.

The telemetry features of the IPG 100 allow the status of the IPG to be checked as noted earlier. For example, when the HHP 202 and/or the CP 204 initiate a programming session with the IPG 100 (FIG. 1), the capacity of the battery is telemetered so that the external programmer can calculate the estimated time to recharge. Any changes made to the current stimulus parameters are confirmed through back telemetry, thereby assuring that such changes have been correctly received and implemented within the implant system. Moreover, upon interrogation by the external programmer, all programmable settings stored within the implant system 10 may be uploaded to one or more external programmers.

Figure 4:
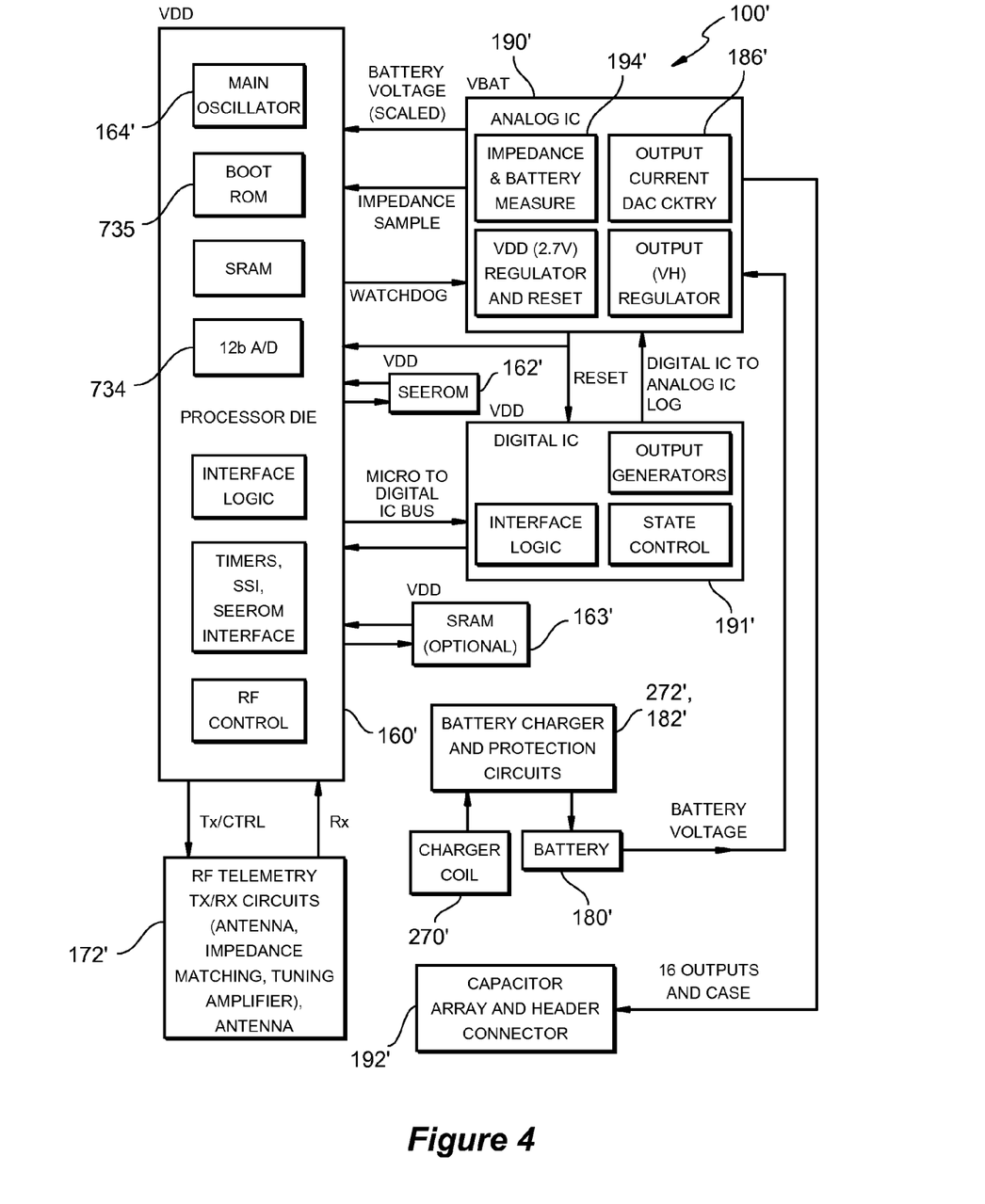
FIG. 4 shows a block diagram that illustrates another embodiment of an implantable stimulator device in which the invention can be used.

Turning next to FIG. 4, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 3. The IPG 100' includes a processor die, or chip, 160', an RF telemetry circuit 172' (typically realized with discrete components), a charger coil 270', a rechargeable battery 180', battery charger and protection circuits 272', 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, SRAM or other memory, two synchronous serial interface circuits, a serial EEPROM interface, and a ROM boot loader 735. The processor die 160' may further include an efficient clock oscillator circuit 164', and (as noted earlier) mixer and modulator/demodulator circuitry implementing the QFAST RF telemetry method. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include output current DAC circuitry 186' configured to supply current to a load, such as tissue, for example. The output current DAC circuitry 186' may be configured to deliver up to 20 mA aggregate and up to 12.7 mA on a single channel in 0.1 mA steps. However, it will be noted that the output current DAC circuitry 186' may be configured to deliver any amount of aggregate current and any amount of current on a single channel, according to one exemplary embodiment.

Regulators for the IPG 100' supply the processor and the digital sequencer with a voltage. Digital interface circuits residing on the analog IC 190' are similarly supplied with a voltage. A programmable regulator supplies the operating voltage for the output current DAC circuitry 186'. The coupling capacitors $C_X$ and electrodes $E_X$, as well as the remaining circuitry on the analog IC 186', may all be housed within the hermetically sealed case of the IPG 100. A feedthrough pin, which is included as part of the header connector 192', allows electrical connection to be made between each of the coupling capacitors $C_N$ and the respective electrodes $E_1$, $E_2$, $E_3$, . . . , or $E_{16}$.

The digital IC (DigIC) 191' functions as the primary interface between the processor 160' and the output current DAC circuitry 186', and its main function is to provide stimulus information to the output current DAC circuitry 186'. The DigIC 191' thus controls and changes the stimulus levels and sequences when prompted by the processor 160'. In an exemplary embodiment, the DigIC 191' comprises a digital application specific integrated circuit (digital ASIC).

With the basic structure of an implantable stimulator understood, focus now shifts to a detailed description of the low-error-rate power-saving telemetry features useable with such an implantable stimulator system.

As noted earlier, even when error detection schemes, such as CRC schemes, are used in the telemetry between an IPG 100 and an external component (e.g., HHP 202 or CP 204), errors can occur. This is in part because CRC schemes are not perfect, and can cause, e.g., false positives. It is desirable to reduce such telemetry error rates in a medical device such as an IPG. Moreover, a desired aspect of an improved telemetry solution will save IPG power, such as by not requiring the entirety of a faulty telemetry block to be received by the IPG.

An embodiment of the disclosed telemetry protocol addresses these problems. To briefly summarize this protocol prior to setting forth its details, the sending device (e.g., an external component such as the HHP 202 or CP 204) forms a block of information to be telemetered in a typical fashion, including a header, the message, and a CRC for that data. This CRC of the block, called CRC1, is preferably computed using a first CRC polynomial. Then, the entirety of the block, including the header, message, and CRC1, is divided into smaller packets of a predetermined byte size. Each packet, regardless of its contents (i.e., regardless of whether it contains the header, the message, or the CRC1, or portions of these), has a CRC computed for it. The CRCs of the packets, called CRC2s, are preferably (but not necessarily) computed using a second CRC polynomial different from the first. So formed, each packet with its appended CRC2 is sent to the receiving device, which deduces a CRC2 and compares it with the appended CRC2. If not valid, that packet is requested to be resent. If valid, the next packet is requested to be sent, its CRC2 checked, etc., until all packets are received and verified. At this point, the receiving device discards the CRC2s from the received packets and reconstitutes the original block (including the header, message, and CRC1). The receiving device then deduces CRC1 and compares it with the CRC1 appended to the block. If valid, the block is accepted, and if not, the procedure is repeated for the block.

Through use of this protocol, improved (1) data integrity, (2) time savings, and (3) power consumption are achieved. Improved data integrity/reduced error rates result from the redundancy involved in calculating two CRCs (CRC1 and CRC2), one on the whole of the block and one on the various packets that comprise the block. Use of different CRC polynomials at these two levels of assessment further reduces error rates, because one polynomial can catch errors another polynomial would miss. However, this is not strictly necessary, and the same CRC polynomial can be used for both CRC1 and CRC2.

Time and power savings result because an entire block need not be received and assessed by the receiving device before a determination of transmission error is made. Instead, at least some transmission errors can be assessed, and remedied, at the packet level, as opposed to the block level. If an error is determined (e.g., via the CRC2 for the packet), only that packet need be retransmitted, rather than the longer block. As a result, the receiving circuitry (e.g., the RF-telemetry circuitry 172) will be powered on less, which saves power in the IPG 100. Moreover, through packetization of the data being transmitted, less memory is needed, which is beneficial particularly on the IPG side of the telemetry, because useable space is limited in the IPG.

Figure 7:
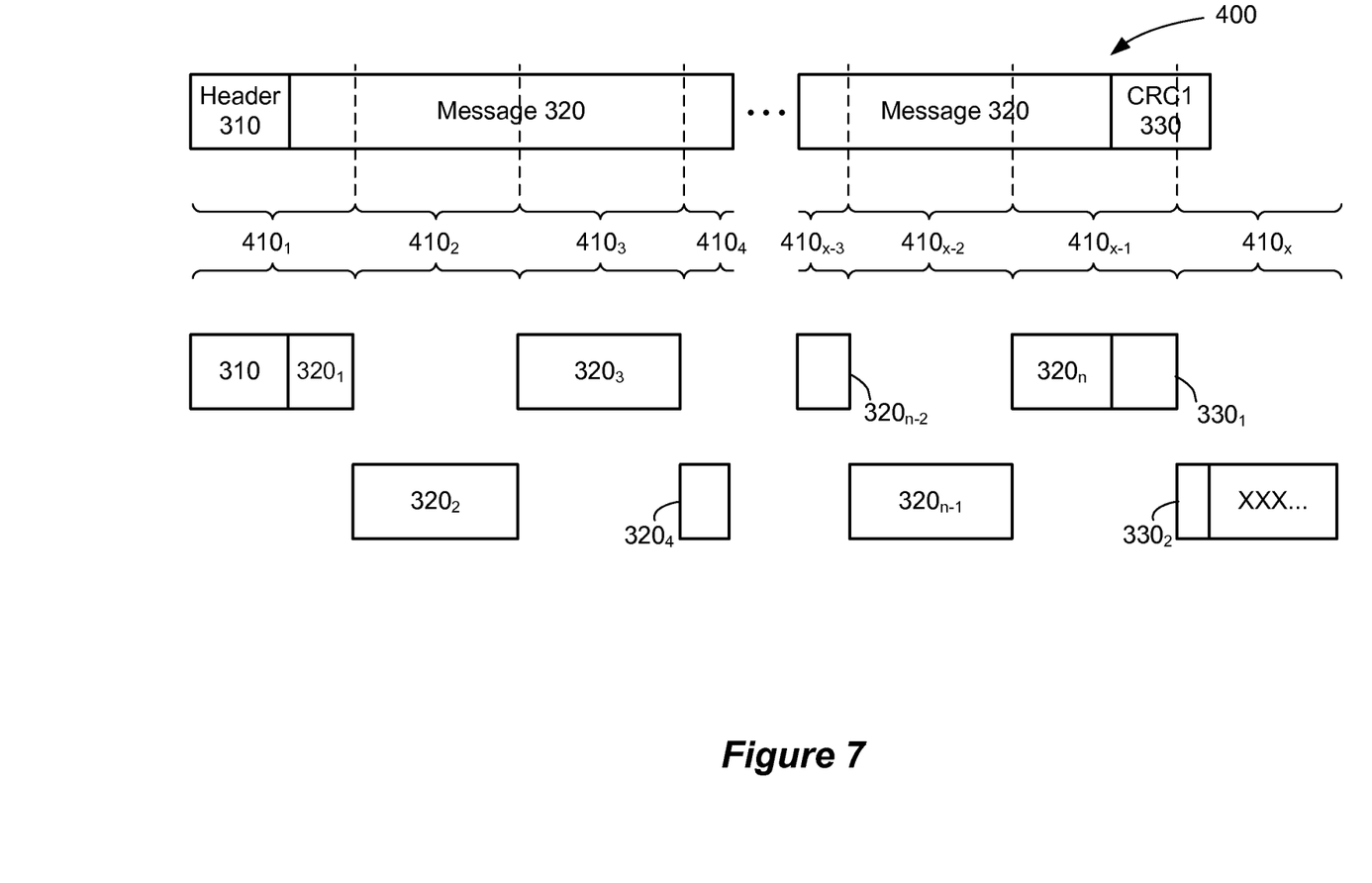
FIG. 7 shows in accordance with an embodiment of the invention how a block of information to be telemetered is divided into packets.
Figure 8:
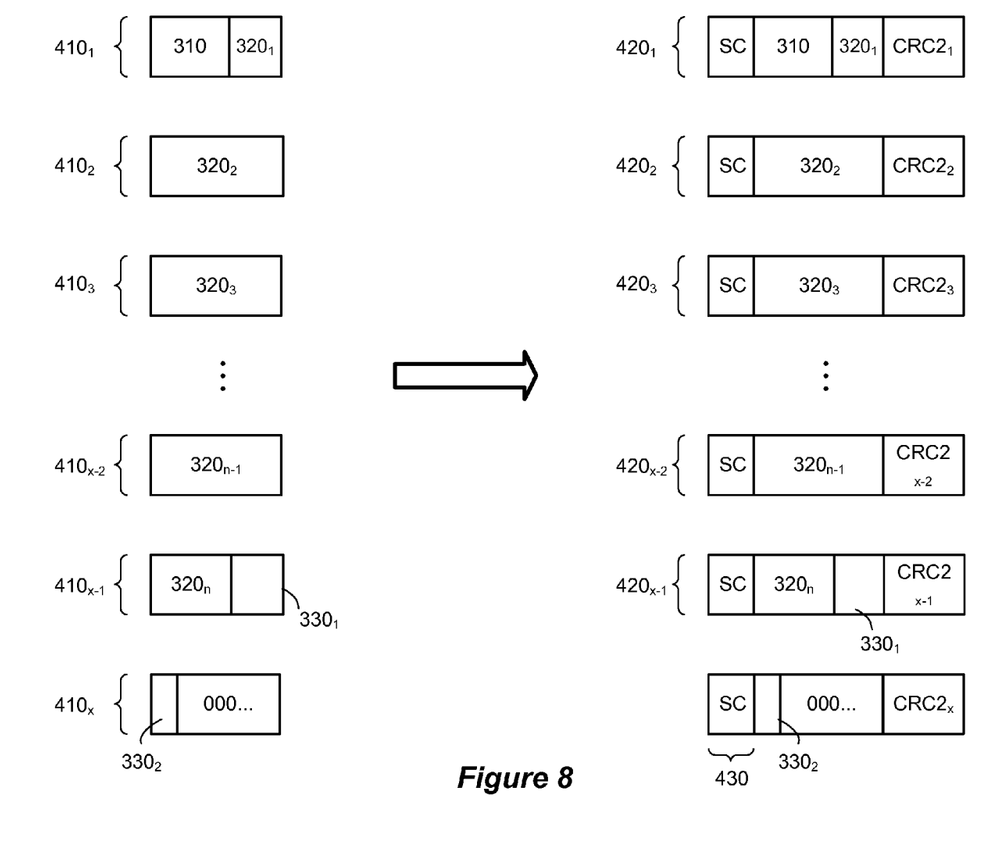
FIG. 8 shows in accordance with an embodiment of the invention how the packets of FIG. 7 are processed to add a CRC to each packet, and to add a packet start code if desired.
Figure 9:
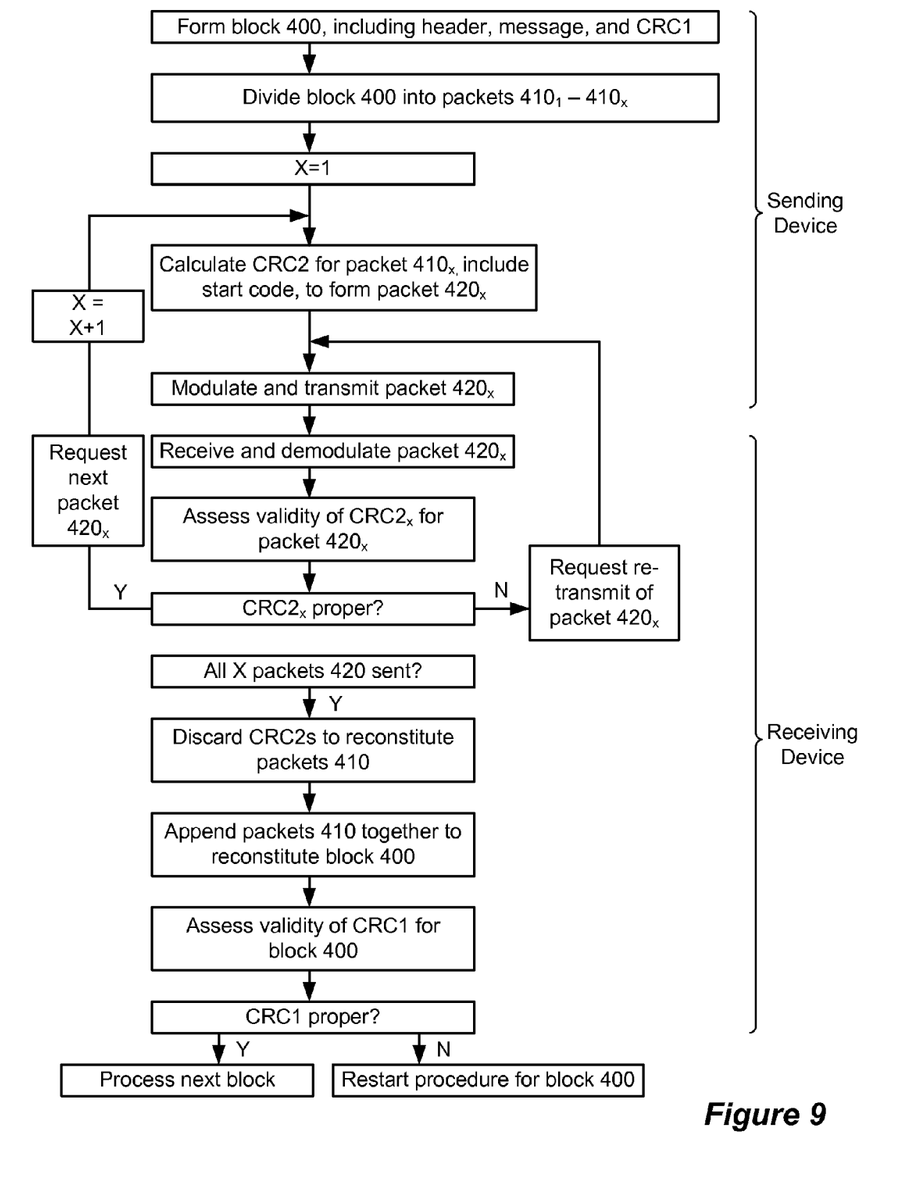
FIG. 9 illustrates a flow chart showing how the packets in FIG. 8 are telemetered between the sending device and the receiving device in an implantable stimulator device system, and specifically notes how the each packet, and ultimately the block they represent, is processed.

Further details of this telemetry protocol are illustrated in FIGS. 7-9. In FIG. 7, a block 400 to be telemetered is compiled by the sending device. The sending device would preferably be the external component, but could also be the IPG, such as when the IPG is communicating to the external component. The block can be similar to blocks of information telemetered in the prior art (FIG. 6), and can include a header 310, a message 320, and CRC 330 information. However, it should be recognized that a header 310 is not strictly necessary, and if present could be considered as part of the message. In a preferred embodiment, the header 310 includes at least an ID number for the IPG to which data is to be telemetered, and is three bytes long. The message 320, which comprises the main data payload to the IPG, and which, e.g., includes the various stimulation parameters for the IPG, can be variable in length, for example, between 2 and 129 bytes.

As noted in the above summary, the CRC 330 comprises a first CRC (i.e., CRC1) used as error detection for the other data in the block 400 (i.e., optional header 310 and at least message 320). The CRC1 can be processed as to just the message 320. However, in a preferred embodiment, the CRC1 is applied to header 310 and the message 320, which would allow data in both of these fields to be assessed for error. Further, the CRC polynomial used to determine CRC1 from the header 310 and message 320 may be any of a large selection of polynomials, such as 0x8005. CRC1 is preferably 2 bytes in length, but may be any length.

In a first step in the telemetry process, the block 400 is divided into packets $410_1$ through $410_x$, where x is as large as needed to fully cover the entirety of the block 400. In a preferred embodiment, each packet 410 is 16 bytes long, although again other sizes can be used. Definition of each 16-byte packet 410 preferably starts at the beginning of the block 400. Because of this, some packets 410 might contain the dividing lines between the various parts of the blocks. Thus, as shown, block $410_1$ contains the entirety of the header 310, but only the first part ($320_1$) of the message. Packet $410_{x-1}$ contains the last part of the message, plus a first part ($330_1$) of the CRC1. The last block $410_x$ contains the last part ($330_2$) of the CRC1 and, because the end of the block has been reached, otherwise contains irrelevant data. Of course, because the size of block 400 is potentially variable, these dividing lines may occur in different places.

In a next step of the telemetry process, the packets 410 are further processed as shown in FIG. 8. Specifically, in a preferred embodiment, additional information is added to each packets 410 to form new packets 420. Specifically, a start code 430 and another CRC (called CRC2 or the packet CRC) are added to each packet 410 to form a corresponding packet 420. The start code 430, as its name reflects, signals the start of the packet 420, and preferably includes a code recognizable by the receiving device to which the packet will ultimately be telemetered to inform of the start of the packet data to follow. Through the use of such a start code 430, the receiving device understands where the actual data in the packet starts and stops, and so alleviates the problem that the receiving device might miss a bit at the beginning of the data sequence, or erroneously add an additional bit at the beginning of the data sequence. In some embodiments, the start code 430 is a single byte (e.g., 01000110; decimal number '70'), or may be smaller or larger, depending on system implementation details. However, while use of a start code 430 is preferred to increase the stability and reliability of the communication between the sending and receiving devices, it is not required in all useful embodiments.

The packet CRC (CRC2) comprises the CRC as run on each of the packets 410 individually. Thus, packet $410_1$'s CRC2 is CRC$2_1$, etc. Each CRC2 can either be calculated for just the original data packet 410, or can additionally include the start code 430. Either way, it is preferred that the CRC2 polynomial be different for that used at the block 400 level, i.e., CRC1. For example, the packet CRC2 may be determined using polynomial 0x1021, although of course other polynomials could be used. By using different CRC polynomials the block (CRC1) and packet (CRC2) levels, errors perhaps not caught by one of the CRCs because of the particular mathematics involved will more likely be caught by the other CRC. However, the same CRC polynomial can be used at each level as well, although this scheme, again depending of the mathematics involved, may not pick up additional errors in a given circumstance. In addition, inclusion of the start code 430 in the CRC2 determination for packets 420 would likely add additional distinguishing data over that available at the block level, and could help ensure that new errors are caught at the packet level, even if the same CRC polynomials are used.

Regardless, once packets 420 are formed, they are ready to be telemetered from the sending device to the receiving device, as illustrated in the flow chart of FIG. 9. It should be noted that the packets 420 can all be formed as shown in FIG. 8 and then telemetered, or the first packet $420_1$ can be formed, then telemetered, followed by formation and telemetry of the second packet $420_2$, etc. Either way, in a preferred embodiment, the packets 420 will be modulated (i.e., at 121 kHz or 129 kHz depending on whether a '0' or '1' is being sent) at the sending device, and demodulated at the receiving device (e.g., using the circuitry of FIG. 5) to retrieve the packets 420 in digital form.

At that point, the receiving device calculates the CRC2 for the first packet $420_1$, and compares it with the CRC2 ($CRC2_1$) appended to that packet $420_1$. If it matches, the receiving device requests the sending device to send the next packet $420_2$. If it does not match, the receiving device requests the sending device to resend the first packet $420_1$. At the sending device, the $CRC2_1$ can either be redetermined to reform the packet $420_1$, or the previously-formed packet $420_1$ can simply be sent again, etc. Either way, using this scheme, a transmission error in a particular packet 420 does not require a resend of the entire block 400, thus saving IPG power.

In a preferred embodiment, each packet 420 is sent and checked by the receiving device before the next packet is sent and checked. This scheme is preferred because if a particular packet 420 cannot be verified as accurate per the CRC2 analysis, that packet can be reconstituted and/or resent by the sending device before the next packet is sent, as just described.

Once the packets 420 have been sent in order, checked via the CRC2s, and resent if necessary, the receiving device now has all of the packets 420 needed to reconstitute the block 400. Thus, the CRC2s, having been used to error check the telemetry of each of the packets 420, can be discarded, along with the start codes (if used) to reconstitute original packets 410. Then the packets 410 are appended together in series to reconstitute the block 400.

At the point, the reconstituted block 400 at the receiving device comprises the header 310 (if used), the message 320, and the CRC1 (which may or may not include assessment of the header 310), as it was first constituted in FIG. 7. With this block now reconstituted, the receiving device can compute the CRC1 for the data (either the message 320 alone or in combination with the header 310), and compare it with that appended to the block 400. If proper, that block is deemed valid, and a next block is processed; if not, the block is once against requested for retransfer.

Thus, although each packet 420 was error checked at the CRC2 level, the reconstituted block 400 is again error checked at the CRC1 level. As noted, this dual-level error-assessment scheme reduces the overall telemetry error rate, particularly when different CRC polynomials are used at the two levels of analysis, and if the start codes 430 are included in the CRC2 calculations.

Further improvements in error rate reduction can be achieved by instituting other measures which attempt to characterize the RF environment in which the implantable stimulator system is operating, and to accordingly permit or exclude telemetry depending on measured characteristics of that environment.

For example, in a preferred embodiment, the external device (e.g., HHP 202 or CP 204) assesses level of noise present in the ambient environment and decides, relative to the strength of its broadcasting signal, whether telemetry to the IPG 100 is warranted. Thus, and as shown in FIG. 1, a noise monitoring circuit 250 interfaces with (or is a part of) either HHP 202 or CP 204. Circuit 250 assesses background level of noise present in the ambient RF environment, and preferably assesses the background noise at those frequencies at which the external components would communicate (e.g., ~125 kHz). The HHP 202, knowing the signal strength of the telemetry at which they will broadcast to the IPG, can then determine whether the signal-to-noise ratio is permissible for reliable communication. If above a preset threshold, telemetry can continue; if not, telemetry may be reserved until a more appropriate time when background noises as measured by circuit 250 are lower. In any event, the addition of such signal-to-noise capability to the sending portions of the implantable stimulator system can further reduce telemetry error rates when used with the telemetry protocols (e.g., the dualistic use of CRC1 and CRC 2) that are disclosed. However, the use of such signal-to-noise circuitry is not required in all embodiments of the invention.

Characterization of the RF environment can also be made on the receiving side of the telemetry. As shown in FIG. 3, squelch circuitry 260 can be employed to determine whether a received packet 420 is suitable for consideration, or is questionable and should be disregarded. Specifically, squelch circuitry 260 provides an indication of the quality of the signal, i.e., signal to noise ratio. If below a user-defined threshold, the telemetry circuitry 172 in the receiving device may request to the sending device that a particular packet be resubmitted, regardless of whether the packet-level CRC2 assessment suggests a problem. But the point remains that an assessment of the signal strength of a received packet on the receiving side of the telemetry can be utilized to infer the reliability of the packets 420 received by the receiving device. Thus, even absent CRC considerations, such packets may be disregarded as unreliable, and such squelch circuitry 260 can be used to further improve the expected telemetry error rates of the external component-implantable stimulator device system.

While the use of Cyclic Redundancy Codes (CRCs) are the preferred error detection scheme, one skilled in the art will recognize that other error detection algorithms could be used with embodiments of the disclosed telemetry protocol. For example, the use of checksums, parity bit checking schemes, or the like could also or instead be used.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method for receiving payload data telemetered between an external component and an implantable medical device, comprising:

receiving a plurality of packets at a receiving device from a sending device, each received packet comprising packet data and second error detection data determined for at least a portion of the packet data;

assessing at least the portion of the packet data using the second error detection data for each received packet at the receiving device, and, if valid, accepting the packet at the receiving device;

forming a block at the receiving device using the accepted packets, the block comprising at least the payload data and first error detection data determined at least for the payload data;

computing a code for the payload data in the block in the receiving device; and comparing the code to the first error detection data in the block to determine whether to accept the block at the receiving device, wherein one of the external component and the implantable medical device comprises the sending device and the other comprises the receiving device.

2. The method of claim 1, wherein the receiving device comprises the implantable medical device.

3. The method of claim 1, wherein the first and second error detection data respectively comprise first and second cyclic redundancy codes.

4. The method of claim 3, wherein the first and second cyclic redundancy codes comprise different cyclic redundancy polynomials.

5. The method of claim 1, wherein the block includes a header for the payload data.

6. The method of claim 5, wherein the code is computed for the payload data and the header.

7. The method of claim 5, wherein the code is computed for the payload data but not the header.

8. The method of claim 1, wherein the received packets comprise start codes, and wherein the second error detection data for each packet is used to assess the portion of the packet data and the start code.

9. The method of claim 1, wherein the received packets comprise start codes, and wherein the second error detection data for each packet is used to assess the portion of the packet data but not the start code.

10. The method of claim 1, wherein the packets are of fixed size.

11. The method of claim 1, wherein assessing at least the portion of the packet data for each received packet comprises determining a code for at least the portion of the packet data for each received packet, and comparing the code to the second error detection data received for that received packet.

12. The method of claim 1, wherein forming the block comprises concatenating at least a portion of the packet data of the accepted packets.

13. The method of claim 12, wherein the block does not include a start code.

14. The method of claim 12, wherein the block does not include the second error detection data for the accepted packets.

15. The method of claim 1, further comprising, if the at least the portion of the packet data is assessed as invalid using the second error detection data for a received packet, requesting to the sending device that the invalid packet be resent to the receiving device.

16. A method for telemetering payload data between an external component and an implantable medical device, comprising:

computing at the sending device first error detection data for at least the payload data to be telemetered to the receiving device;

forming a block at a sending device, the block comprising at least the payload data and the first error detection data determined for at least the payload data;

forming a plurality of packets at the sending device by dividing the block, each packet comprising at least a portion of the block and second error detection data determined for at least that portion of the block; and transmitting the plurality of packets to a receiving device;

wherein one of the external component and the implantable medical device comprises the sending device and the other comprises the receiving device.

17. The method of claim 16, wherein the sending device comprises the external component.

18. The method of claim 16, wherein the first and second error detection data respectively comprise first and second cyclic redundancy codes.

19. The method of claim 18, wherein the first and second cyclic redundancy codes comprise different cyclic redundancy polynomials.

20. The method of claim 16, wherein the formed block includes a header for the payload data.

21. The method of claim 20, wherein the first error detection data is determined for the payload data and the header.

22. The method of claim 20, wherein the first error detection data is determined for the payload data but not the header.

23. The method of claim 16, wherein forming the packets comprises associating a start code with each of the packets.

24. The method of claim 23, wherein the second error detection data is determined for the start code and the portion of the block for each packet.

25. The method of claim 23, wherein the second error detection data is determined for the portion of the block for each packet but not the start code.

26. The method of claim 16, further comprising retransmitting one of the plurality of second packets if requested by the receiving device.

27. The method of claim 16, wherein the packets are of fixed size.

* * * * *